(12) United States Patent
Jain et al.

(10) Patent No.: US 7,228,175 B2
(45) Date of Patent: Jun. 5, 2007

(54) CARDIAC RHYTHM MANAGEMENT SYSTEMS AND METHODS USING ACOUSTIC CONTRACTILITY INDICATOR

(75) Inventors: Mudit Jain, Woodbury, MN (US); Steven L. Higgins, Rancho Santa Fe, CA (US); Scott A. Meyer, Rochester, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 598 days.

(21) Appl. No.: 10/146,479

(22) Filed: May 15, 2002

(65) Prior Publication Data
US 2003/0216620 A1    Nov. 20, 2003

(51) Int. Cl.
*A61N 1/362* (2006.01)
(52) U.S. Cl. ........................................... 607/17
(58) Field of Classification Search ............... 600/300, 600/301; 607/4–28
See application file for complete search history.

(56) References Cited

U.S. PATENT DOCUMENTS

| | | | |
|---|---|---|---|
| 4,357,944 A | 11/1982 | Mauser et al. | 128/663 |
| 4,651,716 A | 3/1987 | Forester et al. | 128/1 D |
| 4,881,549 A | 11/1989 | Rhyne | 128/660.07 |
| 4,917,115 A | 4/1990 | Flammang et al. | 607/19 |
| 4,936,304 A | 6/1990 | Kresh et al. | |
| 5,139,020 A | 8/1992 | Koestner et al. | 128/419 PG |
| 5,156,154 A | 10/1992 | Valenta, Jr. et al. | 128/661.09 |
| 5,156,157 A | 10/1992 | Valenta, Jr. et al. | 128/662 |
| 5,183,040 A | 2/1993 | Nappholz et al. | 128/419 PG |
| 5,188,106 A | 2/1993 | Nappholz et al. | 128/419 PG |
| 5,197,467 A | 3/1993 | Steinhaus et al. | 128/419 PG |
| 5,220,924 A | 6/1993 | Frazin | 128/662.06 |
| 5,243,976 A | 9/1993 | Ferek-Petric et al. | 607/6 |
| 5,305,745 A | 4/1994 | Zacouto | 128/637 |
| 5,316,001 A | 5/1994 | Ferek-Petric et al. | 128/661.08 |
| 5,452,459 A | 9/1995 | Drury et al. | |
| 5,508,045 A | 4/1996 | Harrison et al. | 424/608 |
| 5,527,336 A | 6/1996 | Rosenbluth et al. | 606/192 |
| 5,544,656 A | 8/1996 | Pitsillides et al. | 128/661.04 |

(Continued)

FOREIGN PATENT DOCUMENTS

EP    0503839    9/1992

(Continued)

OTHER PUBLICATIONS

"Realtime Position Management—Tracking Technology", *Cardiac Pathways Corporation*, www.cardiac.com/products_systems.html,(2001),2 pgs. (viewed web site on Apr. 5, 2002).

(Continued)

*Primary Examiner*—Scott M. Getzow
(74) *Attorney, Agent, or Firm*—Schwegman, Lundberg, Woessner, & Kluth, P.A.

(57) ABSTRACT

This document describes systems, devices, and methods that measure a distance between ultrasound or other acoustic transducers to provide a contractility or other therapy efficacy indication. In one example, the indication is communicated to a caregiver for assisting in the caregiver's determination of particular therapy settings. In another example, the indication is used in a feedback controller to automatically adjust one or more therapy parameters based at least in part on the indication.

42 Claims, 9 Drawing Sheets

U.S. PATENT DOCUMENTS

| | | | |
|---|---|---|---|
| 5,546,949 A | 8/1996 | Frazin et al. | 128/662.06 |
| 5,609,612 A | 3/1997 | Plicchi et al. | 607/17 |
| 5,632,032 A | 5/1997 | Ault et al. | |
| 5,657,760 A | 8/1997 | Ying et al. | 128/660.03 |
| 5,676,162 A | 10/1997 | Larson, Jr. et al. | 128/899 |
| 5,676,651 A | 10/1997 | Larson, Jr. et al. | 604/33 |
| 5,693,091 A | 12/1997 | Larson, Jr. et al. | 612/3 |
| 5,702,430 A | 12/1997 | Larson, Jr. et al. | 607/1 |
| 5,722,419 A | 3/1998 | Semmlow et al. | 128/733 |
| 5,727,552 A | 3/1998 | Ryan | 128/653.1 |
| 5,738,096 A | 4/1998 | Ben-Haim | 128/653.1 |
| 5,749,831 A | 5/1998 | Baker | 600/301 |
| 5,752,971 A | 5/1998 | Rosenbluth et al. | 606/192 |
| 5,758,666 A | 6/1998 | Larson, Jr. et al. | 128/899 |
| 5,792,199 A | 8/1998 | Fayram et al. | 607/19 |
| 5,814,599 A | 9/1998 | Mitragotri et al. | 514/3 |
| 5,830,848 A | 11/1998 | Harrison et al. | 514/2 |
| 5,836,985 A | 11/1998 | Rostami et al. | 607/14 |
| 5,843,129 A | 12/1998 | Larson, Jr. et al. | 607/1 |
| 5,865,738 A | 2/1999 | Morcos et al. | 600/365 |
| 5,870,749 A | 2/1999 | Adusumilli | |
| 5,879,375 A | 3/1999 | Larson, Jr. et al. | 607/30 |
| 5,892,950 A | 4/1999 | Rigori et al. | |
| 5,925,069 A | 7/1999 | Graves et al. | 607/36 |
| 5,941,978 A | 8/1999 | Finni | |
| 5,948,771 A | 9/1999 | Danziger | 514/185 |
| 5,953,530 A | 9/1999 | Rishi et al. | |
| 5,974,438 A | 10/1999 | Neufeld | |
| 5,991,660 A | 11/1999 | Goyal | 607/14 |
| 6,023,579 A | 2/2000 | Hellgren et al. | |
| 6,024,703 A | 2/2000 | Zanelli et al. | 600/437 |
| 6,042,614 A | 3/2000 | Davidson et al. | |
| 6,085,240 A | 7/2000 | Suzuki et al. | |
| 6,176,883 B1 | 1/2001 | Holloway et al. | |
| 6,202,199 B1 | 3/2001 | Wygodny et al. | |
| 6,205,482 B1 | 3/2001 | Navarre et al. | |
| 6,208,345 B1 | 3/2001 | Sheard et al. | |
| 6,209,018 B1 | 3/2001 | Ben-Shachar et al. | |
| 6,216,027 B1 | 4/2001 | Willis et al. | 600/424 |
| 6,247,039 B1 | 6/2001 | Callsen | |
| 6,277,077 B1 | 8/2001 | Brisken et al. | 600/459 |
| 6,282,579 B1 | 8/2001 | Carre | |
| 6,282,701 B1 | 8/2001 | Wygodny et al. | |
| 6,289,393 B1 | 9/2001 | Phillips et al. | |
| 6,298,269 B1 * | 10/2001 | Sweeney | 607/28 |
| 6,317,428 B1 | 11/2001 | Mercouroff et al. | |
| 6,321,337 B1 | 11/2001 | Reshef et al. | |
| 6,324,648 B1 | 11/2001 | Grantges, Jr. | |
| 6,330,598 B1 | 12/2001 | Beckwith et al. | |
| 6,378,124 B1 | 4/2002 | Bates et al. | |
| 6,378,125 B1 | 4/2002 | Bates et al. | |
| 6,398,736 B1 | 6/2002 | Seward | 600/466 |
| 6,421,565 B1 | 7/2002 | Hemmingsson | 607/17 |
| 6,443,894 B1 | 9/2002 | Sumanaweera et al. | 600/443 |
| 6,445,776 B1 | 9/2002 | Shank et al. | |
| 6,450,977 B1 | 9/2002 | Baxter-Jones | 600/591 |
| 6,467,052 B1 | 10/2002 | Kaler et al. | |
| 6,491,639 B1 | 12/2002 | Turcott | 600/508 |
| 6,496,833 B1 | 12/2002 | Goldberg et al. | |
| 6,530,079 B1 | 3/2003 | Choi et al. | |
| 6,539,262 B2 | 3/2003 | Sweeney | 607/28 |
| 6,539,501 B1 | 3/2003 | Edwards | |

FOREIGN PATENT DOCUMENTS

| | | |
|---|---|---|
| EP | 0503285 | 10/1992 |
| WO | WO-95/19806 | 7/1995 |
| WO | WO-98/38911 | 9/1998 |
| WO | WO-99/07285 | 2/1999 |

OTHER PUBLICATIONS

Ben-Haim, Shlomo A., "Catheter Navigation in Modern Electrophysiology", *Journal of Cardiovascular Electrophysiology*, vol., No. 11, (Nov. 2000),1193-1195.

De Groot, Natasja M., et al., "Three-Dimensional Catheter Positioning During Radiofrequency Ablation in Patients: First Application of a Real-Time Position Management System", *Journal of Cardiovascular Electrophysiology*, vol. 11, No. 11,, (Nov. 2000),1183-1192.

"Realtime Position Management—Tracking Technology", *Cardiac Pathways Corporation*, www.cardiac.com/products_systems.html,(2001),2 pgs.

* cited by examiner

CARDIAC RHYTHM MANAGEMENT SYSTEMS AND METHODS USING ACOUSTIC CONTRACTILITY INDICATOR

TECHNICAL FIELD

This document relates generally to medical systems, devices, and methods, and particularly, but not by way of limitation, to cardiac rhythm management systems and methods using an acoustic contractility indicator.

BACKGROUND

When functioning properly, the human heart maintains its own intrinsic rhythm. Its sinoatrial node generates intrinsic electrical cardiac signals that depolarize the atria, causing atrial heart contractions. Its atrioventricular node then passes the intrinsic cardiac signal to depolarize the ventricles, causing ventricular heart contractions. These intrinsic cardiac signals can be sensed on a surface electrocardiogram (ECG) obtained from electrodes placed on the patient's skin, or from electrodes implanted within the patient's body. The surface ECG waveform, for example, includes artifacts associated with atrial depolarizations ("P-waves") and those associated with ventricular depolarizations ("QRS complexes").

A normal heart is capable of pumping adequate blood throughout the body's circulatory system. However, some people have irregular cardiac rhythms, referred to as cardiac arrhythmias. Moreover, some patients have poor spatial coordination of heart contractions. In either case, diminished blood circulation may result. For such patients, a cardiac rhythm management system may be used to improve the rhythm and/or spatial coordination of heart contractions. Such systems are often implanted in the patient and deliver therapy to the heart.

Cardiac rhythm management systems include, among other things, pacemakers, also referred to as pacers. Pacers deliver timed sequences of low energy electrical stimuli, called pace pulses, to the heart, such as via an intravascular lead wire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly. Such pacers may also coordinate atrial and ventricular contractions to improve pumping efficiency.

Cardiac rhythm management systems also include cardiac resynchronization therapy (CRT) devices for coordinating the spatial nature of heart depolarizations for improving pumping efficiency. For example, a CRT device may deliver appropriately timed pace pulses to different locations of the same heart chamber to better coordinate the contraction of that heart chamber, or the CRT device may deliver appropriately timed pace pulses to different heart chambers to improve the manner in which these different heart chambers contract together.

Cardiac rhythm management systems also include defibrillators that are capable of delivering higher energy electrical stimuli to the heart. Such defibrillators include cardioverters, which synchronize the delivery of such stimuli to sensed intrinsic heart activity signals. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering a high energy electrical stimulus that is sometimes referred to as a defibrillation countershock, also referred to simply as a "shock." The countershock interrupts the tachyarrhythmia, allowing the heart to reestablish a normal rhythm for the efficient pumping of blood. In addition to pacers, CRT devices, and defibrillators, cardiac rhythm management systems also include devices that combine these functions, as well as monitors, drug delivery devices, and any other implantable or external systems or devices for diagnosing or treating the heart.

One problem presented by some cardiac patients is determining the extent of any benefit obtained from a particular cardiac resynchronization therapy (e.g., left ventricular pacing, bi-ventricular pacing, and/or multisite pacing within the same heart chamber), or parameter settings controlling such therapy. This may include determining whether a patient is actually benefitting from the CRT or other therapy being received. This may also include determining whether a particular CRT or other therapy benefits a particular patient more or less than another different CRT or other therapy. For these and other reasons, the present inventors have recognized that there exists an unmet need for improved techniques of determining the efficacy of such therapy.

SUMMARY

This document discusses, among other things, systems, devices, and methods that measure a distance between ultrasound or other acoustic transducers to provide a contractility or other therapy efficacy indication. In one example, the indication is communicated to a caregiver for assisting in the caregiver's determination of particular therapy settings. In another example, the indication is used in a feedback controller to automatically adjust one or more therapy parameters based at least in part on the indication.

In one example, this document describes a system that includes first and second acoustic transducer interfaces. The first acoustic transducer interface is configured to be coupled to a first acoustic transducer located in or about a heart. The second acoustic transducer interface is configured to be coupled to a second acoustic transducer. A controller circuit is coupled to the first and second acoustic transducer interfaces to measure a distance, between the first and second acoustic transducers, that varies during a heart contraction. The controller is configured to provide an indication based on a variation of the distance during at least one heart contraction.

In another embodiment, this document describes a method. The method includes transmitting, at a first location, an acoustic signal through a portion of a pump. The acoustic signal is received at a second location. A change in distance between the first and second locations is determined during at least one pump contraction. A "contractility" or other indication is provided, based at least in part on a degree of the change in the distance between the first and second locations during the at least one pump contraction.

Other aspects of the discussed systems, devices, and methods will become apparent upon reading the following detailed description and viewing the drawings that form a part thereof.

BRIEF DESCRIPTION OF THE DRAWINGS

In the drawings, which are offered by way of example, and not by way of limitation, and which are not necessarily drawn to scale, like numerals describe substantially similar components throughout the several views. Like numerals having different letter suffixes represent different instances of substantially similar components.

DETAILED DESCRIPTION

In the following detailed description, reference is made to the accompanying drawings, which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

This document discusses, among other things, systems, devices, and methods that will be described in applications involving implantable medical devices including, but not limited to, implantable cardiac rhythm management systems such as pacemakers, cardioverter/defibrillators, pacer/defibrillators, biventricular or other multi-site resynchronization or coordination devices, and drug delivery systems. However, these systems, devices, and methods may be employed in unimplanted devices, including, but not limited to, external pacemakers, cardioverter/defibrillators, pacer/defibrillators, biventricular or other multi-site resynchronization or coordination devices, monitors, programmers and recorders, whether such devices are used for providing a diagnostic, a therapy, or both a diagnostic and a therapy.

Figure 1:
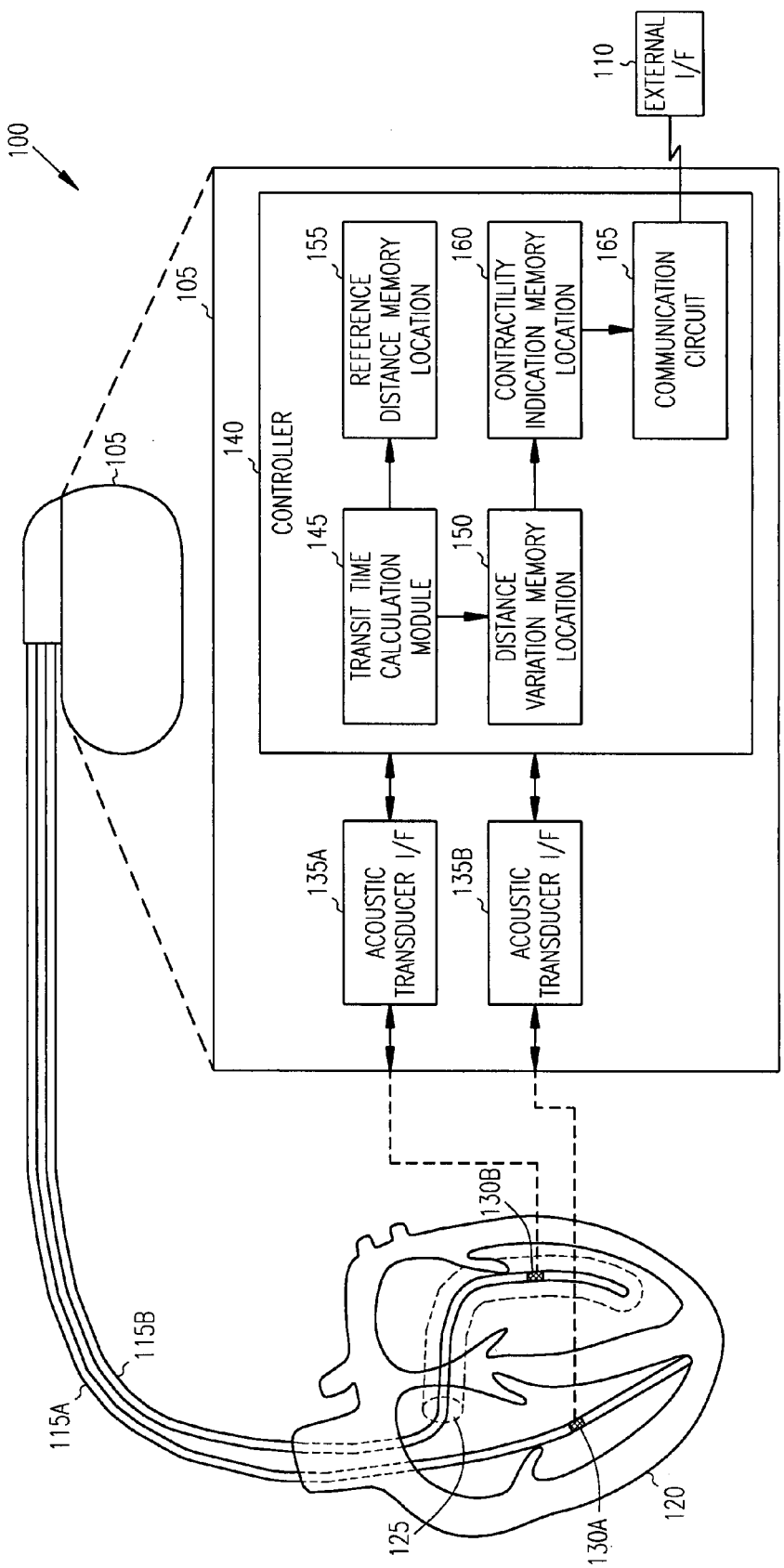
FIG. 1 is a schematic diagram illustrating generally an example of portions of a cardiac rhythm management system providing a therapy efficacy indication based on a measured distance between acoustic transducers.

FIG. 1 is a schematic diagram illustrating generally, by way of example, but not by way of limitation, portions of a cardiac rhythm management system 100 providing a therapy efficacy indication based on a measured distance between acoustic transducers. System 100 includes a hermetically sealed implantable cardiac rhythm management device 105 and a programmer or other external interface 110. In this example, intracardiac leads 115A–B are catheters connected to device 105, with respective distal portions intravascularly introduced into heart 120. In the illustrative example of FIG. 1, a distal portion of lead 115A is introduced into a right ventricle of heart 120, and a distal portion of lead 115B is introduced through coronary sinus 125 (which, in this document, includes the great cardiac vein) into proximity with a wall of a left ventricle of heart 120. Leads 115A–B include respective ultrasound or other acoustic transducers 130A–B. Transducers 130A–B are respectively disposed in the right ventricle and in proximity to the left ventricle (e.g., within coronary sinus 125), such that at least one of transducers 130A–B undergoes motion during a ventricular heart contraction. In one example, leads 115A–B also include one or more pacing and/or defibrillation electrodes, such as for providing pacing, resynchronization, cardioversion, and/or defibrillation therapy to heart 120.

In the example of FIG. 1, device 105 carries various electrical components, such as ultrasonic or other acoustic transducer interfaces 135A–B. Transducer interfaces 135A–B are electrically connected to respective transducers 130A–B via wires extending from device 105 through respective leads 115A–B. Transducer interfaces 135A–B collectively include circuits for transmitting an acoustic signal at one of transducers 130A–B and detecting a received acoustic signal at the other one of transducers 130A–B. Device 105 also includes controller circuit 140, which is coupled to transducer interfaces 135A–B. In one example, controller 140 is capable of sequencing through various control states such as, for example, by using a digital microprocessor having executable instructions stored in an associated instruction memory circuit, a microsequencer, or a state machine. However, controller 140 is capable of using many other hardware/firmware/software implementations.

In the example of FIG. 1, controller 140 includes a transit time calculation module 145 to calculate the transit time of the acoustic signal transceived between transducers 130A–B. Based on the calculated transit time, and the known velocity of the ultrasound or other acoustic signal in the surrounding media (e.g., heart tissue, blood, and/or other bodily fluids), controller 140 calculates a distance between transducers 130A–B. Controller 140 calculates how much the distance between transducers 130A–B varies during a heart contraction (or averaged over several heart contractions), such as by performing several individual distance calculations during a single heart contraction to determine an amplitude of the distance variation. This distance variation is stored in a distance variation memory location 150. In one example, this distance variation may, but need not, be computed with respect to a previously-computed reference distance between transducers 130A–B, which is stored in a reference distance memory location 155.

Figure 2:
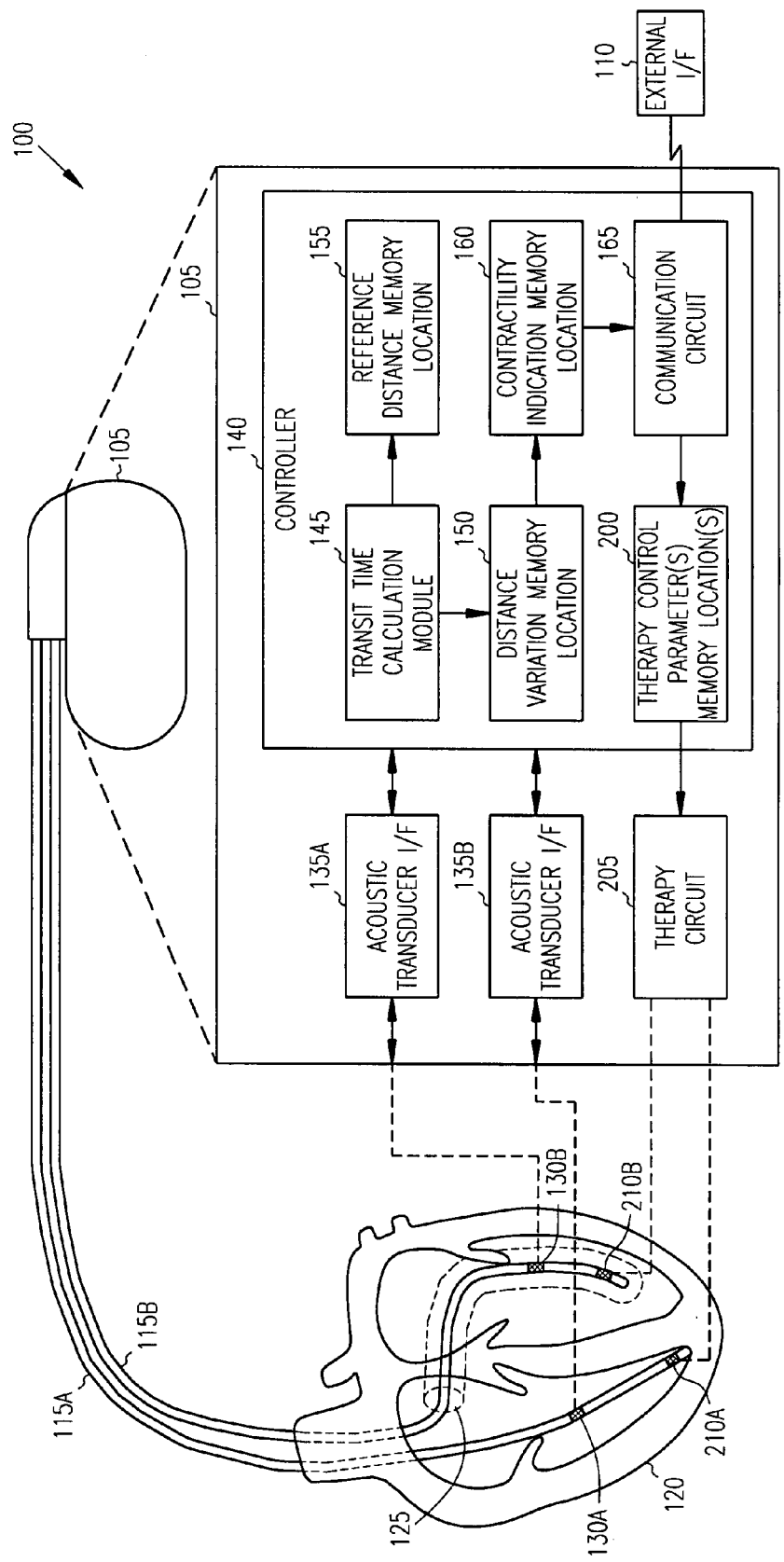
FIG. 2 is a schematic diagram illustrating generally an example of portions of a cardiac rhythm management system including at least one therapy control parameter capable of being based on the therapy efficacy indication.

The distance variation between transducers 130A–B provides, among other things, a resulting indication of the contractility of heart 120, which is stored in a contractility indication memory location 160. In one example, a wireless telemetry or other communication circuit 165 communicates the contractility indication to a second communication circuit in a programmer or other external interface 110, such as for display on a graphical user interface (GUI) to a physician or other caregiver. Using the displayed contractility indication as an indicator of the efficacy of therapy being provided to heart 120 (e.g., pacing and/or cardiac resynchronization therapy), the caregiver communicates particular values of one or more therapy control parameters (e.g., rate, electrode selection, interelectrode delay, etc.) from external interface 110 to device 105, to be stored in one or more therapy control parameter memory locations 200, as illustrated in the schematic diagram of FIG. 2. In this example, the therapy control parameters control operation of a pacing and/or cardiac resynchronization therapy circuit 205, which is coupled to right ventricular (RV) electrode 210A and left ventricular (LV) electrode 210B. In one example, electrical stimuli are delivered to heart 120 via electrodes 210A–B to coordinate the timing of RV and LV contractions, such as in a patient with congestive heart failure (CHF), to increase cardiac output. In a further example, an interelectrode delay between the RV and LV stimuli associated with the same heart contraction instance is adjusted by the caregiver using efficacy information determined from the contractility indication received at external interface 110 from device 105. The caregiver adjusts the value of the interelectrode delay parameter stored in therapy control parameter memory location(s) 200 such that an increased acute or chronic contractility indication is obtained. In one example, therefore, contractility indication memory location 160 includes several memory locations, such as for logging contractility data over an extended period of time (e.g., between a patient's visits to the caregiver).

Figure 3:
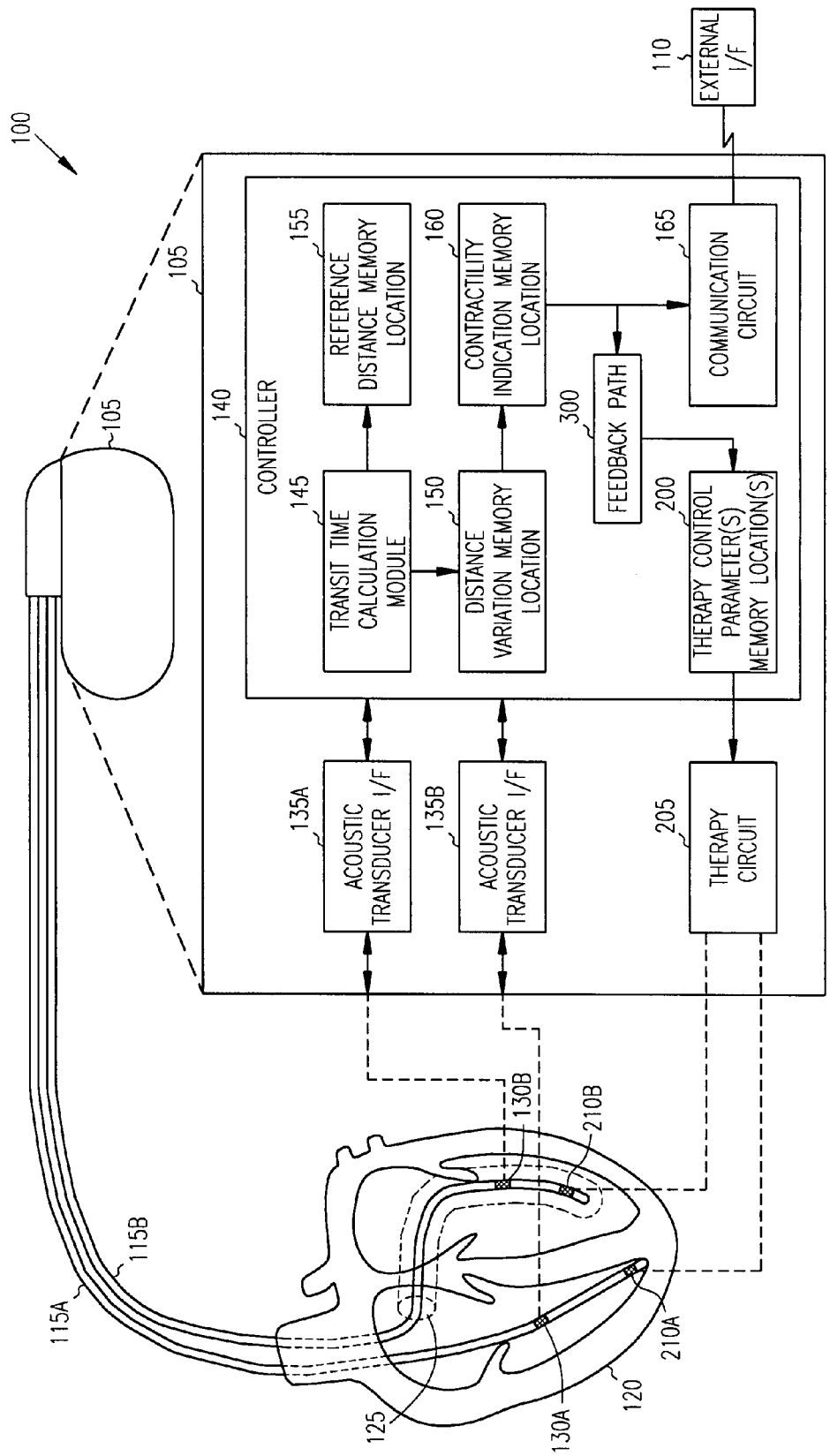
FIG. 3 is a schematic diagram illustrating generally an example of portions of a cardiac rhythm management system including at least one therapy control parameter capable of being substantially automatically based on the therapy efficacy indication.
Figure 9:
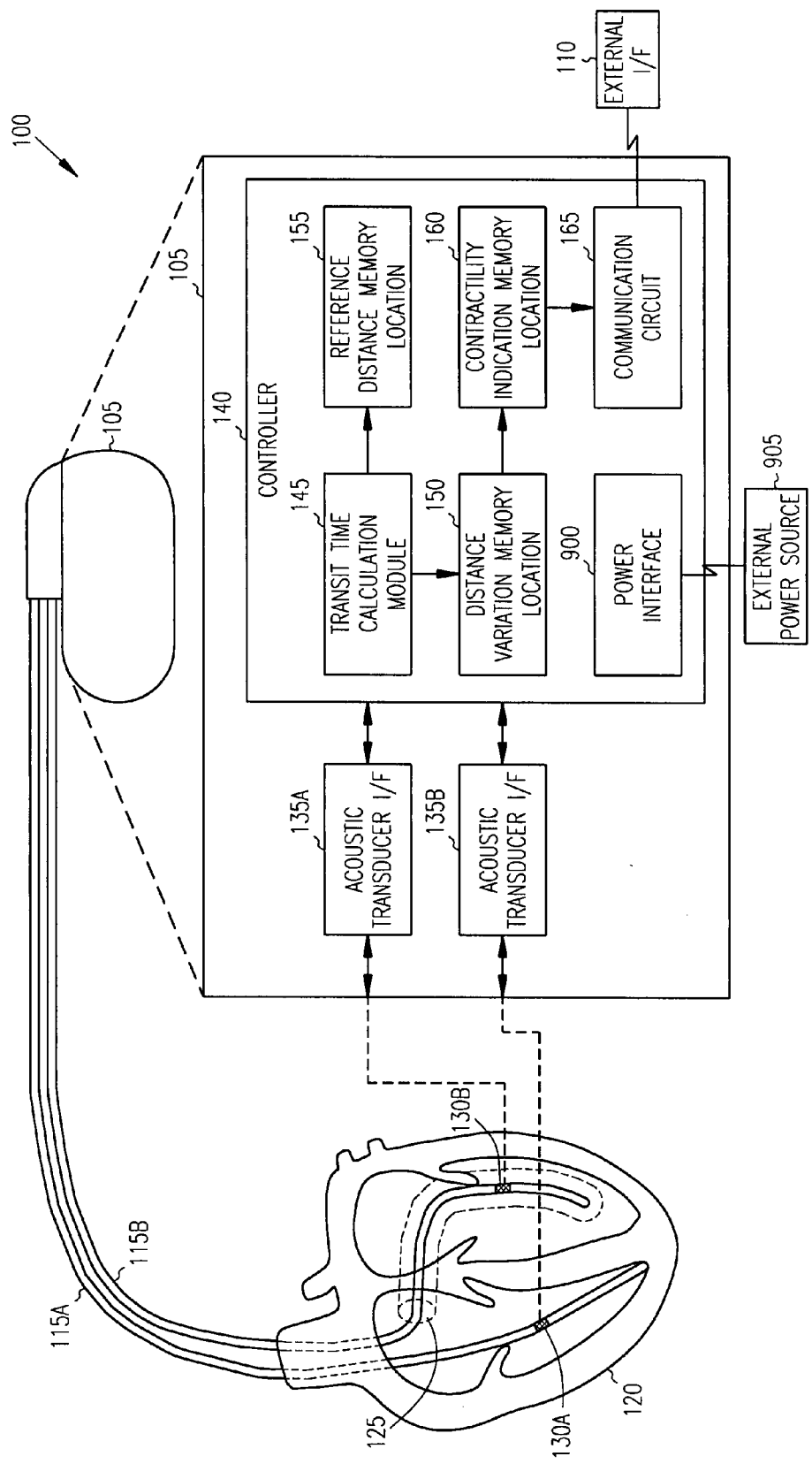
FIG. 9 is a schematic diagram illustrating generally one example of a device including a power interface.

FIG. 3 is a schematic diagram illustrating generally another example, in which device 105 includes a feedback path 300 that uses the contractility indication as at least one basis for automatically occasionally or frequently adjusting one or more values stored in therapy control parameter memory location(s) 200. This, in turn, adjusts how cardiac resynchronization or other therapy is delivered to heart 120. Therapy efficacy is monitored using the distance measurement between acoustic transducers 130A–B for further adjusting one or more therapy parameters using this feedback loop. To reduce power consumption, the distance measurement between acoustic transducers 130A–B is, in one example, performed infrequently, and acoustic transducer interfaces 135A–B are powered off or down during the time periods between such infrequent measurements. In another example, device 105 wirelessly (or otherwise) receives at least some power (e.g., inductively coupled onto communication circuit 165 from external interface 110) from an external power source, either during such acoustic monitoring, or to recharge a battery included in device 105 between and/or during instances of such monitoring. In this manner, the received power energizes (or assists in energizing) acoustic transducers 130A–B and/or associated acoustic transducer interfaces 135A–B, or otherwise compensates for at least a portion of the power consumption of such components. The power may, but need not, be received by communication circuit 165; FIG. 9 is a schematic diagram illustrating generally another example in which device 105 includes a coil or other power interface 900—separate from communication circuit 165—for wirelessly (or otherwise) receiving power from another coil or other external power source 905. The received power at least partially energizes (or compensates for the power consumption of) one or more of acoustic transducers 130A–B and/or associated acoustic transducer interfaces 135A–B.

Figure 4:
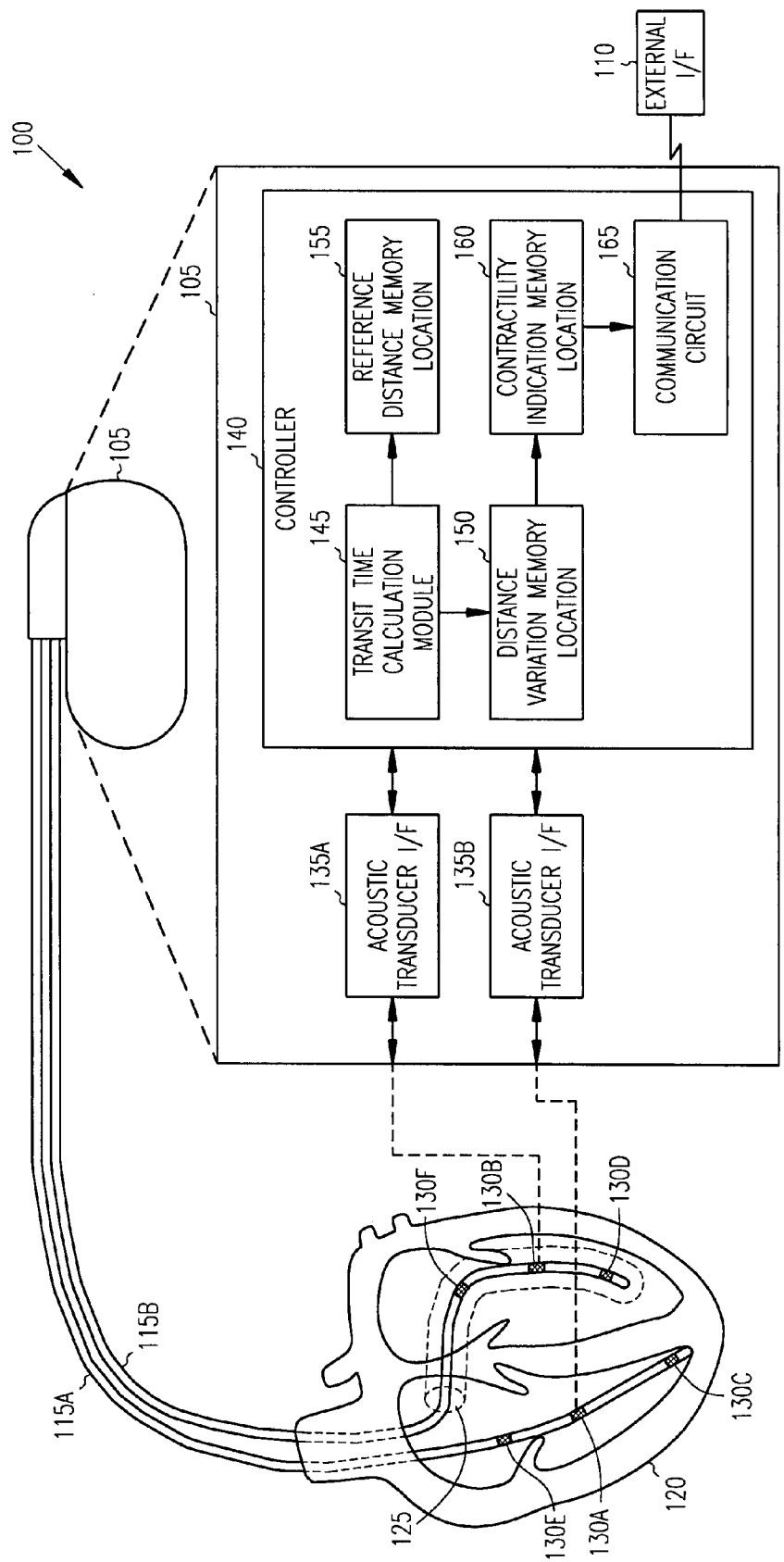
FIG. 4 is a schematic diagram illustrating generally an example of portions of a cardiac rhythm management system including further acoustic transducers.

FIG. 4 is a schematic diagram illustrating generally, by way of example, but not by way of limitation, further acoustic transducers 130C–F, variously disposed on leads 115A–B or elsewhere (e.g., epicardially or even externally, such as in contact with the skin of the patient). These further acoustic transducers are either multiplexed to acoustic transducer interfaces 135A–B or connected to additional acoustic transducer interfaces. In one example, such multiple transducers 130A–F are used to calculate one or more reference distances between pairs of transducers 130A–F (e.g., using triangulation techniques), which are then stored in reference distance memory locations 155. Heart contraction distance variations between such pairs of transducers 130A–F may, but need not, then be computed with respect to the corresponding stored reference distance. In another example, one or more such additional transducer pairs are used to provide additional distance variation measurements. In one example, such additional distance variation measurements provide localized contractility information between particular different cardiac regions of interest. In another example, such additional distance variation measurements are combined (after any optional weighting) to provide a distributed indication of cardiac contractility.

Figure 5:
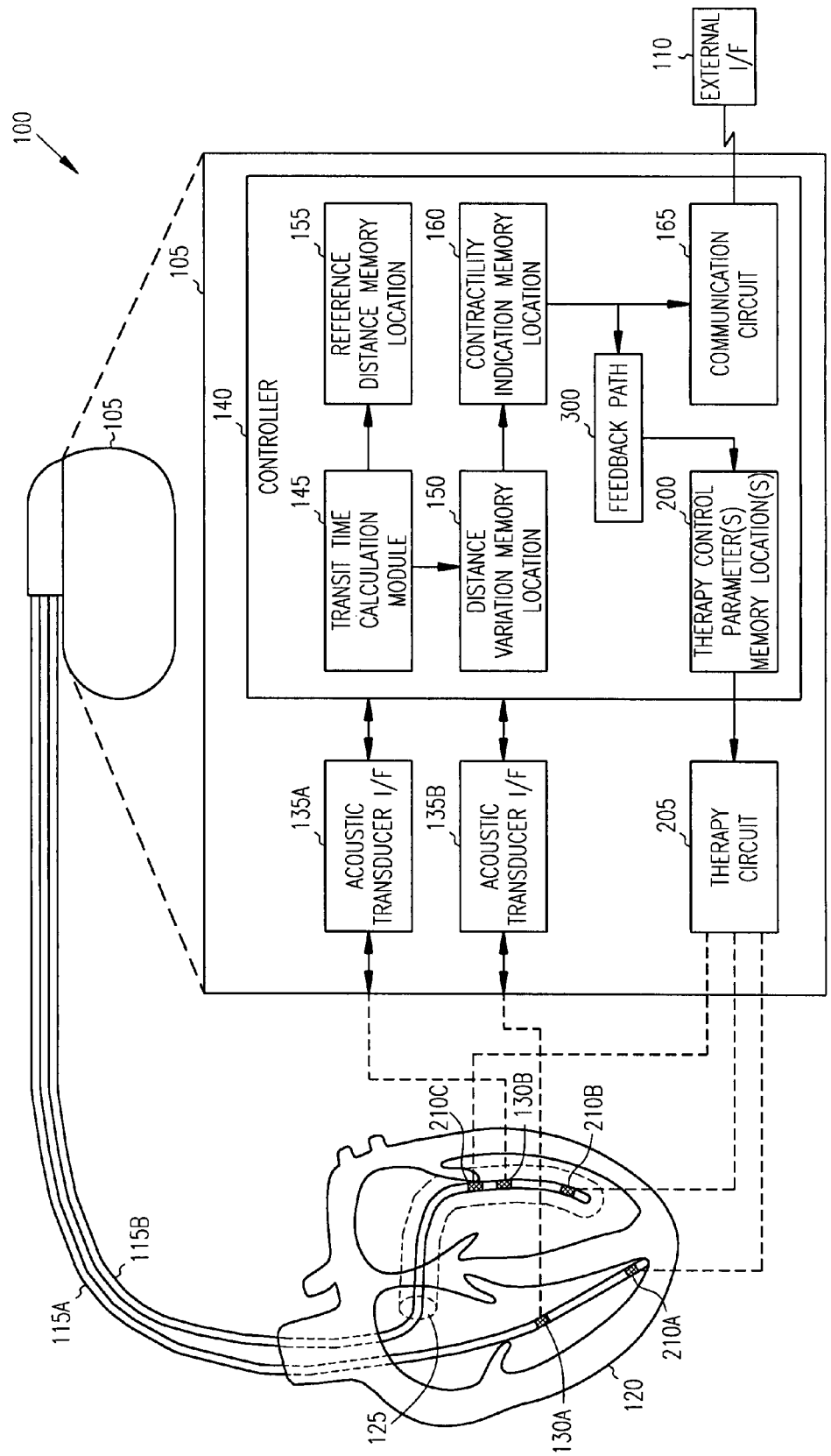
FIG. 5 is a schematic diagram illustrating generally an example of portions of a cardiac rhythm management system including electrodes capable of being selected for delivering therapy based at least in part on the therapy efficacy indication.

FIG. 5 is a schematic diagram illustrating generally further example including one or more additional electrodes, such as electrode 210C disposed within coronary sinus 125 in proximity to the left ventricle. In one example, one therapy control parameter that is adjusted in response to a contractility indication of cardiac resynchronization therapy efficacy is a parameter that controls which electrode(s) are used to deliver such therapy. In this example, the distance between ultrasound transducers 130A–B is monitored, and the resulting contractility-based therapy efficacy indication is used to select which two (or all three) of electrodes 210A–C is used to deliver resynchronizing electrical stimuli to heart 120. In a further example, the efficacy indication is additionally used to determine the value(s) of interelectrode delays between the selected two or three electrodes (or other number of electrodes, such as in an example in which additional electrodes are present).

Figure 6:
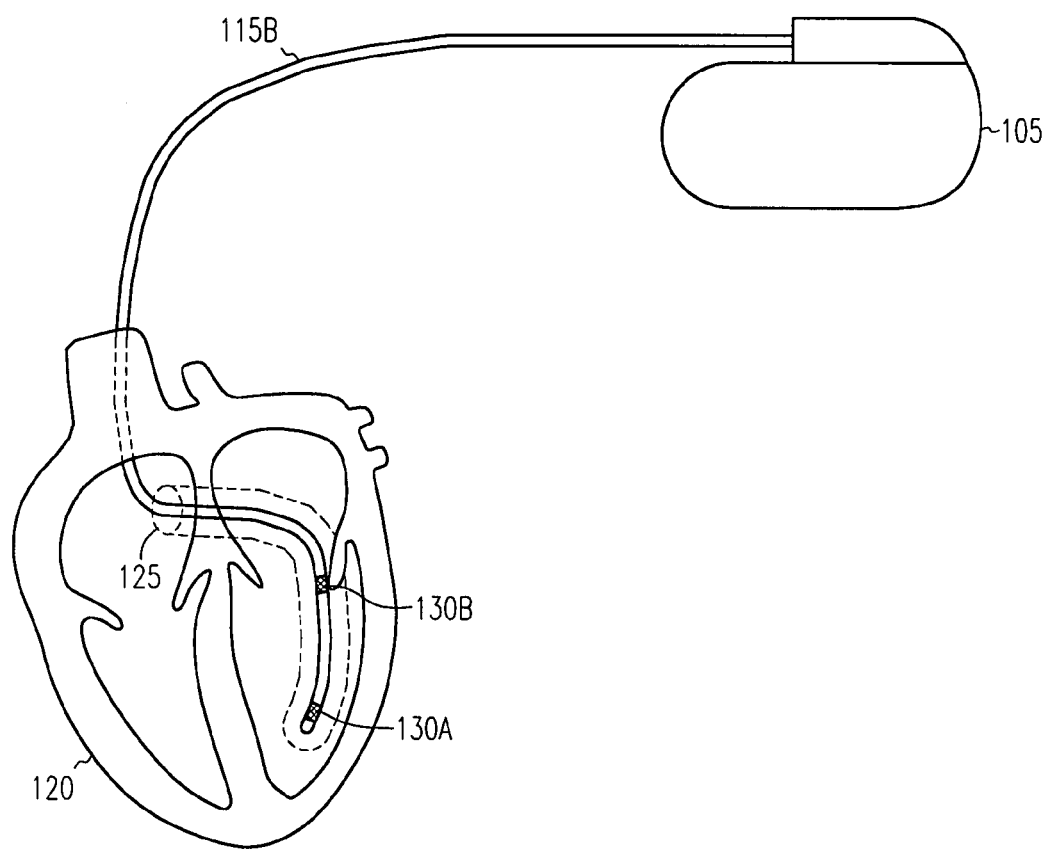
FIG. 6 is a schematic diagram illustrating generally an example having acoustic transducers associated with the same heart chamber, such as the left ventricle.
Figure 7:
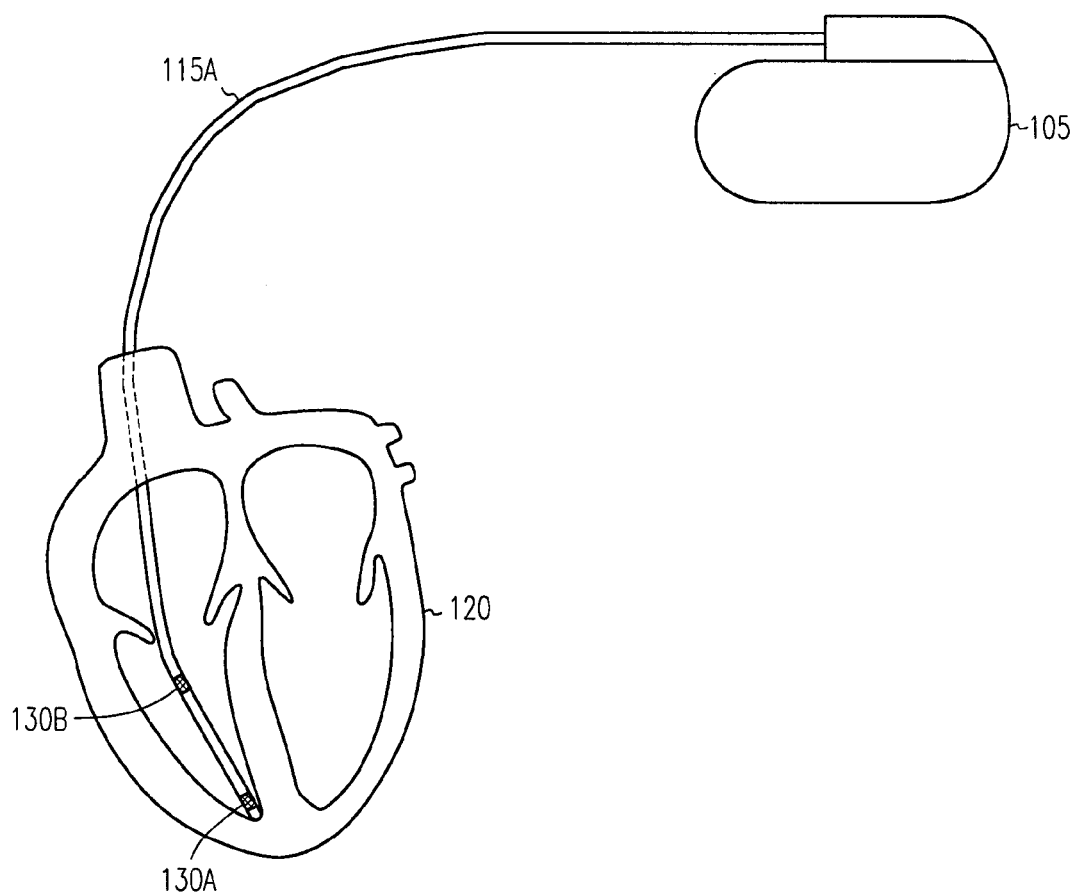
FIG. 7 is a schematic diagram illustrating generally another example having acoustic transducers associated with the same heart chamber, such as the right ventricle.
Figure 8:
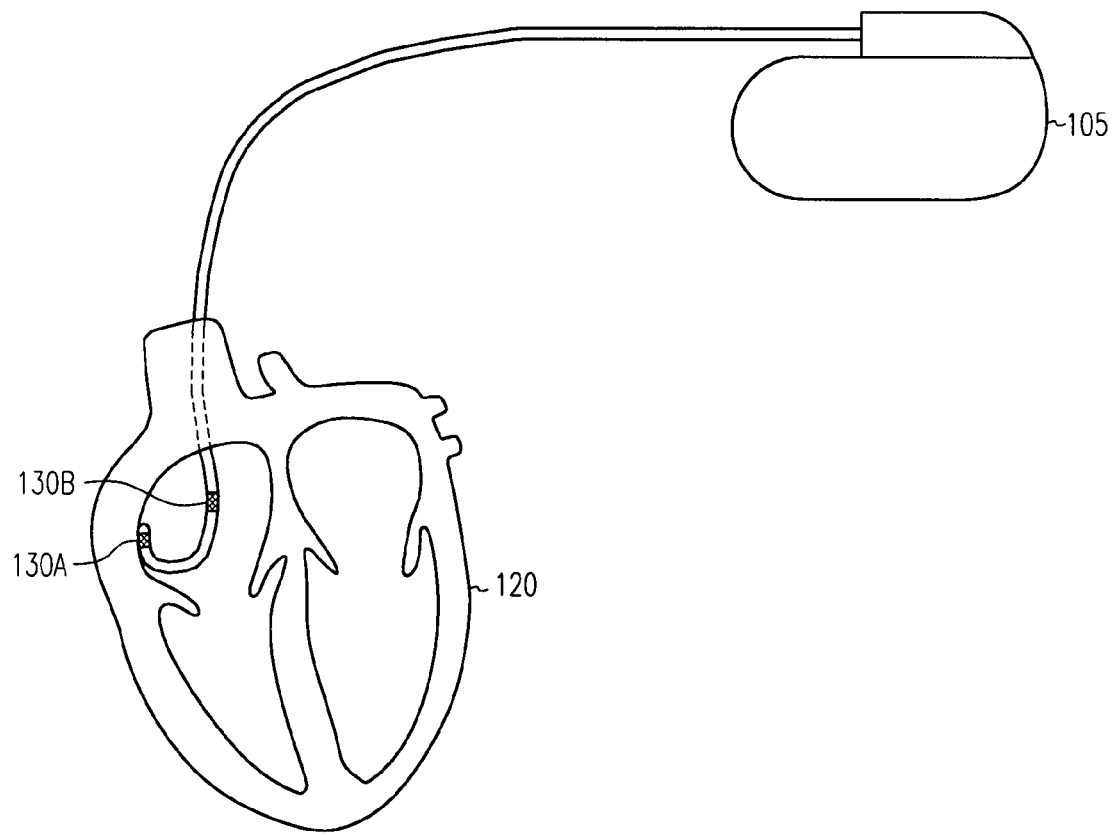
FIG. 8 is a schematic diagram illustrating generally another example having acoustic transducers associated with the same heart chamber, such as the right atrium.

Although the above examples have illustrated acoustic transducers 130A–B located in different heart chambers on separate leads, in other examples, acoustic transducers 130A–B will be located in the same heart chamber, on different leads, or even on the same lead, as illustrated in the example of FIG. 6. In the schematic diagram of FIG. 6, a first acoustic transducer 130A is located more apically within coronary sinus of heart 125, and a second acoustic transducer 130B is located more in a more basal position near the left ventricular free wall. In this example, transducer 130A is expected to undergo less movement during a heart contraction than transducer 130B. FIG. 7 illustrates another example in which both transducers 130A–B are located within the right ventricle for obtaining a contractility indication based on the distance therebetween. FIG. 8 illustrates a further example, in which both transducers are located within a particular atrium (e.g., the right atrium, in the illustration of FIG. 8) for obtaining an atrial contractility indication based on the distance therebetween. Many other locations of acoustic transducers within heart 120, on heart 120, or about heart 120, or even external to the patient.

It is to be understood that the above description is intended to be illustrative, and not restrictive. For example, the above-discussed examples may be used in combination with each other. Many other embodiments will be apparent to those of skill in the art upon reviewing the above description. The scope of the invention should, therefore, be determined with reference to the appended claims, along with the full scope of equivalents to which such claims are entitled. Moreover, the terms "first," "second," "third," etc. are used merely as labels, and are not intended to impose numeric requirements on their objects.

What is claimed is:

1. A system comprising:
    first and second acoustic transducer interfaces, the first acoustic transducer interface configured to be coupled to a first acoustic transducer located in or about right side of a heart, the second acoustic transducer interface configured to be coupled to a second acoustic transducer located in or about a left side of the heart;
    a controller circuit, coupled to the first and second acoustic transducer interfaces to measure a distance, between the first and second acoustic transducers, that varies during a heart contraction, the controller configured to provide a contractility indication based on a variation of the distance during at least one heart contraction; and
    a first communication circuit configured for communicating to an external interface the contractility indication.

2. The system of claim 1, further comprising the first and second acoustic transducers.

3. The system of claim 2, in which the first transducer is disposed on a first intracardiac lead.

4. The system of claim 3, in which the second transducer is disposed on a second intracardiac lead.

5. The system of claim 4, in which the first and second intracardiac leads are different intracardiac leads.

6. The system of claim 4, in which one of the first and second intracardiac leads is sized and shaped to be introduced into a coronary sinus of the heart.

7. The system of claim 6, in which the other of the first and second intracardiac leads is sized and shaped to be introduced into a right ventricle of the heart.

8. The system of claim 2, in which the first and second transducers are ultrasound transducers.

9. The system of claim 1, in which the controller is configured to measure the distance using a transit time of a signal between the first and second acoustic transducers.

10. The system of claim 1, in which the controller is configured to measure the variation of the distance during the at least one heart contraction with respect to a reference distance.

11. The system of claim 10, in which the controller is configured to measure the reference distance using triangulation.

12. The system of claim 1, further comprising:
    a therapy circuit to deliver therapy to the heart; and
    a memory location, coupled to the controller, to store at least one parameter to control operation of the therapy circuit, the at least one parameter based at least in part on the variation of the distance during at least one heart contraction.

13. The system of claim 12, further comprising a feedback circuit, coupled to the controller and the memory location, to store a value of the at least one parameter based at least in part on the variation of the distance during the at least one heart contraction.

14. A system comprising:
    first and second acoustic transducer interfaces, the first acoustic transducer interface configured to be coupled to a first acoustic transducer located in or about a heart, the second acoustic transducer interface configured to be coupled to a second acoustic transducer; and
    a controller circuit, coupled to the first and second acoustic transducer interfaces to measure a distance, between the first and second acoustic transducers, that varies during a heart contraction, the controller configured to provide an indication based on a variation of the distance during at least one heart contraction; and
    an implantable device, comprising the first and second acoustic transducer interfaces and the controller, the implantable device comprising a first communication circuit configured for communicating to a remote external interface the indication based on the variation of the distance during at least one heart contraction.

15. The system of claim 14, further comprising the remote external interface comprising a second communication circuit to communicate with the implantable device for receiving the indication based on the variation of the distance during at least one heart contraction.

16. The system of claim 14, in which the remote external interface includes the second communication circuit to further communicate with the implantable device to store in the memory location the value of the at least one parameter that is based at least in part on the variation of the distance during the at least one heart contraction.

17. A system comprising:
    first and second acoustic transducer interfaces, the first acoustic transducer interface configured to be coupled to a first acoustic transducer located in or about a heart, the second acoustic transducer interface configured to be coupled to a second acoustic transducer; and
    a controller circuit, coupled to the first and second acoustic transducer interfaces to measure a distance, between the first and second acoustic transducers, that varies during a heart contraction, the controller configured to provide an indication based on a variation of the distance during at least one heart contraction; and
    an implantable device, comprising the first and second acoustic transducer interfaces and the controller, the implantable device comprising a power interface to receive power from an external power source to compensate for power consumed by at least one of the first and second transducer interfaces.

18. A system comprising:
    first and second acoustic transducer interfaces, the first acoustic transducer interface configured to be coupled to a first acoustic transducer located in or about a right side of a heart, the second acoustic transducer interface configured to be coupled to a second acoustic transducer located in or about a left side of the heart;
    means for measuring a distance, between the first and second acoustic transducers, that varies during a heart contraction;
    means for providing a contractility indication based on a variation of the distance during at least one heart contraction; and
    a first communication circuit configured for communicating to an external interface the contractility indication.

19. The system of claim 18, further comprising the first and second acoustic transducers.

20. The system of claim 18, further comprising:
a therapy circuit to deliver therapy to the heart; and
a memory location, coupled to a controller, to store at least one parameter to control operation of the therapy circuit, the at least one parameter based at least in part on the variation of the distance during at least one heart contraction.

21. A system comprising:
first and second acoustic transducer interfaces, the first acoustic transducer interface configured to be coupled to a first acoustic transducer located in or about a heart, the second acoustic transducer interface configured to be coupled to a second acoustic transducer;
means for measuring a distance, between the first and second acoustic transducers, that varies during a heart contraction;
means for providing a contractility indication based on a variation of the distance during at least one heart contraction; and
an implantable device, comprising the first and second acoustic transducer interfaces, the means for measuring the distance, and the means for providing the contractility indication, the implantable device further comprising a first communication circuit configured for communicating to a remote external interface the indication based on the variation of the distance during at least one heart contraction.

22. The system of claim 21, further comprising a remote external interface comprising a second communication circuit to communicate with the implantable device for receiving the indication based on the variation of the distance during at least one heart contraction.

23. A system comprising:
an elongate first catheter, comprising a distal portion sized and shaped to be intravascularly introduced into a right ventricle of a heart, the distal portion of the first catheter comprising an ultrasonic first transducer;
an elongate second catheter, comprising a distal portion sized and shaped to be intravascularly introduced into a coronary sinus of the heart, the distal portion of the second catheter comprising an ultrasonic second transducer; and
an implantable cardiac rhythm management device, comprising:
first and second acoustic transducer interfaces, configured to be respectively coupled to the first and second transducers;
a controller circuit, coupled to the first and second acoustic transducer interfaces to measure a distance, between the first and second acoustic transducers, that varies during a heart contraction, the controller configured to provide a contractility indication based on a variation of the distance during at least one heart contraction; and
a first communication circuit configured for communicating to an external interface the contractility indication.

24. The system of claim 23, in which the implantable device further includes:
a therapy circuit to deliver therapy to the heart; and
a memory location, coupled to the controller, to store at least one parameter to control operation of the therapy circuit, the at least one parameter based at least in part on the variation of the distance during at least one heart contraction.

25. A system comprising:
an elongate first catheter, comprising a distal portion sized and shaped to be intravascularly introduced into a right ventricle of a heart, the distal portion of the first catheter comprising an ultrasonic first transducer;
an elongate second catheter, comprising a distal portion sized and shaped to be intravascularly introduced into a coronary sinus of the heart, the distal portion of the second catheter comprising an ultrasonic second transducer; and
an implantable cardiac rhythm management device, comprising:
first and second acoustic transducer interfaces, configured to be respectively coupled to the first and second transducers;
a controller circuit, coupled to the first and second acoustic transducer interfaces to measure a distance, between the first and second acoustic transducers, that varies during a heart contraction, the controller configured to provide an indication based on a variation of the distance during at least one heart contraction; and
in which the implantable device further includes a first communication circuit configured for communicating to a remote external interface the indication based on the variation of the distance during at least one heart contraction.

26. The system of claim 25, further comprising a remote external interface comprising a second communication circuit to communicate with the implantable device for receiving the indication based on the variation of the distance during at least one heart contraction.

27. A system comprising:
a hermetically-sealed implantable cardiac rhythm management device housing comprising:
first and second acoustic transducer interfaces, the first acoustic transducer interface configured to be coupled to a first acoustic transducer located in or about a heart, the second acoustic transducer interface configured to be coupled to a second acoustic transducer;
a controller circuit, coupled to the first and second acoustic transducer interfaces to measure a distance, between the first and second acoustic transducers, that varies during a heart contraction, the controller configured to provide an indication based on a variation of the distance during at least one heart contraction;
a therapy circuit to deliver therapy to the heart;
a memory location, coupled to the controller, to store at least one parameter to control operation of the therapy circuit, the at least one parameter based at least in part on the variation of the distance during at least one heart contraction; and
a first communication circuit configured for communicating to a remote external interface an indication of the at least one parameter based at least in part on the variation of the distance during at least one heart contraction.

28. The system of claim 27, in which the memory location includes a parameter to select at least one particular electrode for delivering therapy.

29. The system of claim 27, in which the memory location includes a parameter to determine a delay between at least one pair of electrodes in delivering stimuli associated with a single ventricular heart contraction.

30. The system of claim 27, further comprising an elongate first catheter, comprising a distal portion sized and shaped to be intravascularly introduced into a heart, the distal portion of the first catheter comprising an ultrasonic first transducer.

31. The system of claim 30, further comprising an elongate second catheter, comprising a distal portion sized and shaped to be intravascularly introduced into the heart, the distal portion of the second catheter comprising an ultrasonic second transducer.

32. A method comprising:
   transmitting, at a first location in a first side of a pump, an acoustic signal through a portion of the pump;
   receiving, at a second location in a second side of the pump, the acoustic signal;
   determining a change in a distance between the first and second locations during at least one pump contraction; and
   providing a contractility indication that is based at least in part on a degree of the change in the distance between the first and second locations during the at least one pump contraction; and
   communicating the contractility indication from within a body to a location outside of the body.

33. The method of claim 32, further comprising communicating the contractility indication from within a body to a remote interface external to the body.

34. The method of claim 33, further comprising receiving from the external interface a pump control parameter that is based at least in part on the contractility indication.

35. The method of claim 33, further comprising displaying the contractility indication.

36. The method of claim 32, further comprising adjusting a pump control parameter based at least in part on the contractility indication.

37. The method of claim 32, in which the determining the change in the distance includes:
   determining a reference distance using triangulation; and
   determining the change in the distance, between the first and second locations during at least one pump contraction, with respect to the reference distance.

38. The method of claim 32, in which the determining the change in the distance includes using a transit time of the acoustic signal to determine a distance between transmitting and receiving acoustic transducers.

39. The method of claim 32, further comprising wirelessly receiving power from a remote power source to compensate for at least a portion of power used in the transmitting and receiving acoustic signals.

40. A method comprising:
   transceiving an ultrasound signal between a first location in a right ventricle and a second location in a coronary sinus;
   determining a distance between the first and second locations based on a transit time of the ultrasound signal;
   determining a change in the distance between the first and second locations during at least one pump contraction; and
   providing a contractility indication that is based at least in part on a degree of the change in the distance between the first and second locations during the at least one pump contraction.

41. The method of claim 40, further comprising adjusting a therapy parameter based at least in part on the contractility indication.

42. The method of claim 41, further comprising providing therapy based on the adjusted therapy parameter.

* * * * *